United States Patent
Rosowsky et al.

(10) Patent No.: US 7,256,197 B2
(45) Date of Patent: Aug. 14, 2007

(54) METHODS FOR SYNTHESIS OF DIARYLMETHANES

(75) Inventors: Andre Rosowsky, Needham, MA (US); Han Chen, Waltham, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 28 days.

(21) Appl. No.: 10/824,321

(22) Filed: Apr. 12, 2004

(65) Prior Publication Data

US 2004/0267011 A1 Dec. 30, 2004

Related U.S. Application Data

(63) Continuation of application No. PCT/US02/32476, filed on Oct. 10, 2002.

(60) Provisional application No. 60/328,879, filed on Oct. 12, 2001.

(51) Int. Cl.
*C07D 239/72* (2006.01)
*A61K 31/517* (2006.01)
*A61P 33/02* (2006.01)
*A61P 33/08* (2006.01)

(52) U.S. Cl. .................... 514/266.1; 544/283

(58) Field of Classification Search ............... 544/283; 514/266.1

See application file for complete search history.

(56) References Cited

U.S. PATENT DOCUMENTS 3,674,825 A 7/1972 Fitton et al.
6,274,587 B1 8/2001 Holladay et al.

OTHER PUBLICATIONS

Snyder et al., J. Med. Liban 48(4): 208-214, 2000.*
Broughton et al. Antimicrobial Agents and Chemotherapy, 1348-1355, 1991.*

* cited by examiner

*Primary Examiner*—Venkataraman Balasubramanian
(74) *Attorney, Agent, or Firm*—Edwards Angell Palmer & Dodge LLP; Peter F. Corless; Mark D. Russett

(57) ABSTRACT

The present invention relates to dihydrofolate reductase inhibitors having an aromatic group and a heteroaromatic group linked by a methylene group; methods of preparation of dihydrofolate reductase inhibitors that include metal mediated cross coupling of an aromatic halide or heteroaromatic halide with an organozinc reagent; and methods of treatment and pharmaceutical compositions that utilize or comprise one or more of such dihydrofolate reductase inhibitors.

13 Claims, No Drawings

METHODS FOR SYNTHESIS OF DIARYLMETHANES

CROSS-REFERENCE TO RELATED APPLICATION(S)

This application is a continuation of copending international patent application PCT/US02/32476, filed on Oct. 10, 2002, which application designates the U.S. and claims priority from U.S. Provisional Application Ser. No. 60/328,879, filed on Oct. 12, 2001.

This invention was made with government support under Grant RO1-I-29904 from the National Institute of Allergy and Infectious Disease, NIH, DHHS. The government has certain rights in the invention.

BACKGROUND OF THE INVENTION

1. Field of the Invention

The present invention provides a new method for the formation of functionalized aryl-alkyl bonds, particularly aryl-aralkyl bonds. In particular, the invention provides methods of synthesizing active dihydrofolate reductase (DHFR) inhibitors and new classes of DHFR inhibitors particularly where a substituted aryl group is linked to a diamino substituted heterocyclic moiety via a methylene group.

2. Background

Piritrexim (1), a lipophilic inhibitor of the key metabolic enzyme dihydrofolate reductase (DHFR) has been studied intensively as an anticancer drug, and more recently was identified as a potent inhibitor of the enzyme from *Pneumocystis carinii* (Pc) and *Tozoplasma gondii* (Tg), two opportunistic parasites known to be potentially life-threatening in patients with acquired immunodeficiency syndrome (AIDS). See, for example, Grivsky, E. M.; Lee, S.; Sigel, C. W.; Duch, D. S.; Nichol, C. A. *J. Med Chem.* 1980; 23, 327-329; Sigel, C. W.; Macklin, A. W.; Woolley, J. L., Jr.; Johnson N. W.; Collier, M. A.; Blum, M. R.; Clendeninn, N. J.; Everitt, J. M.; Grebe, G.; Mackars, A.; Foss, R. G.; Duch, D. S.; Bowers, S. W.; Nichol, C. A. *NCI Monogr.* 1987; 5, 111-120; Laszlo, J.; Brenckman, W. D., Jr.; Morgan, E.; Clendeninn, N. J.; Williams, T.; Currie, V.; Young, C. *NCI Monogr.* 1987; 5, 121-125; and Kovacs, J.; Allegra, C. A.; Swan, J. C.; Drake, J. C.; Parrillo, J. E.; Chabner, B. A.; Masur, H. *Antimicrob. Agents Chemother.* 1988; 32, 430-433. A notable structural feature of 1 is the short CH$_2$ bridge between the two halves of the molecule. This bridge is also present in trimethoprim (2), another lipophilic DHFR inhibitor widely used to for anti-Pc and anti-Tg prophylaxis and therapy in AIDS patients, usually in combination with a sulfa drug to enhance efficacy. For an excellent historical account of the chemical and pharmaceutical development of the older lipophilic DHFR inhibitors pyrimethamine and trimethoprim, see: Roth, B.; Cheng, C. C. *Progr. Med Chem.* 1982; 19, 269-331; Fischl, M. A.; Dickinson, G. M.; La Voie, L. *J. Am. Med. Assoc.* 1988; 259, 1185-1189; and Medina, I.; Mills, J.; Leoung, G.; Hopewell, P. C.; Lee, B.; Modin, G.; Benowitz, N.; Wofsy, C. B. N. *Engl. J Med* 1990; 323, 776-782. Two other members of this class that have been used clinically against these infections are pyrimethamine (3), in which the two halves of the molecule are linked without a CH$_2$ bridge, and trimetrexate (4), which contains a longer CH$_2$NH bridge. In addition to the fact that it contains a longer bridge, 4 differs from 1 in being a quinazoline as opposed to a pyrido[2,3-d]pyrimidine. See for example, Bertino, J. R.; Sawicki, W. L.; Moroson, B. A.; Cashmore, A. R.; Elslager, E. F. *Biochem. Pharmacol.* 1979; 28, 1983-1987; Elslager, E. F.; Johnson, E. L.; Werbel, L. M. *J. Med Chem.* 1983; 26, 1753-1760; and Sattler, F. R.; Frame, P.; Davis, R.; Nichols, L.; Shelton, B.; Akil, B.; Baugman, R.; Hughlett, C.; Weiss, W.; Boylen, C. T.; van der Horst, C.; Black, J.; Masur, H.; Feinberg, J. *J. Infect. Dis.* 1994; 170, 165-172.

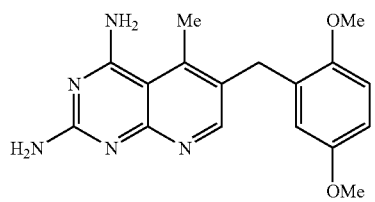

1

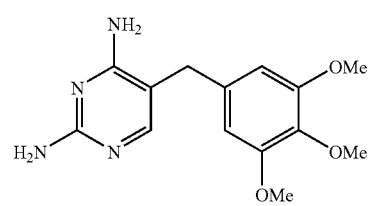

2

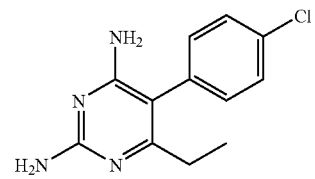

3

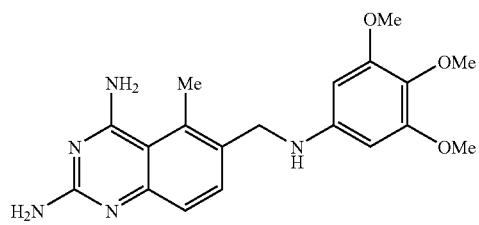

4

There has been reported examples of certain lipophilic DHFR inhibitors in which the fused 2,4-diaminopyrimidine ring system and the aryl side chain are separated by a short O or S bridge, as in 5 and 6. The only quinazoline antifolates reported to date, however, in which the bridge is CH$_2$ are the 5,6,7,8-tetrahydro derivatives 7. See for example Elslager, E. F.; Clarke, J.; Johnson, J.; Werbel, L. M. Davoll, J. *J. Heterocycl. Chem.* 1972; 9, 759-773; Hynes, J. B.; Ashton, W. T.; Merriman, H. G., III, Walker, F. C., III. *J. Med Chem.* 1974; 17, 682-684; and Rosowsky A; Papoulis, A. T.; Forsch, R. A.; Queener, S. F. *J. Med Chem.* 1999; 42, 1007-1017.

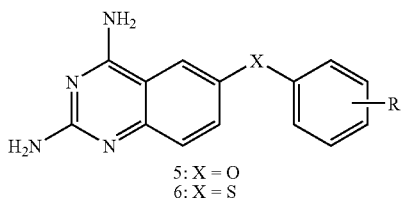

5: X = O
6: X = S

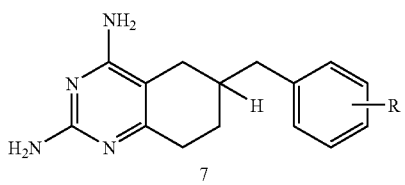

7

It would be desirable to have new methods for synthesis of biologically active DHFR inhibitors.

SUMMARY OF THE INVENTION

We have now discovered metal-mediated methods of forming compounds of the general formula Ar—R where Ar is a carbocyclic aryl group or a heteroaryl group which may be optionally substituted and R is an aralkyl group such as optionally substituted benzyl optionally substituted arylmethyl or optionally substituted heteroarylmethyl.

Methods of the invention provide for the formation of the Ar—R bond by cross-coupling of an aryl halide or a heteroaryl halide, Ar—X where X is typically Br, I or a halide equivalent and an organozinc species, RZnY where R is an aralkyl group such as optionally substituted benzyl, optionally substituted arylmethyl or optionally substituted heteroarylmethyl and Y is an anionic ligand such as F, Cl, Br, I, sulfonate, acetate or amido, wherein the cross-coupling is catalyzed by a metal catalyst such as a group 9 or group 10 complex, preferably the metal catalyst is a nickel, palladium or platinum complex, particularly palladium complexes. Particularly preferred RZnX compounds are organozinc halides, especially RZnCl species.

The present invention also features compounds according to Formula I:

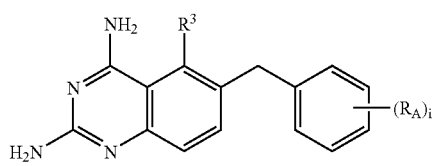

wherein:

$R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, $C_{1-4}$fluoroalkyl, amino, mono and di($C_{1-6}$alkyl) amino, nitrile, optionally substituted aryloxy, optionally substituted heteroaryloxy, $C_{1-6}$alkylthio, optionally substituted arylthio, optionally substituted heteroarylthio, optionally substituted aryl acetoxy or optionally substituted heteroaryl acetoxy; or two adjacent $R_A$ groups taken in combination to form a group of the formula:

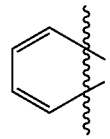

which may be optionally substituted;

$R^3$ is hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, $C_{1-6}$alkylthio, optionally substituted arylthio, or optionally substituted aralkylthio; and i is an integer from 0 to about 5.

Preferred compounds of Formula I are inhibitors of dihydrofolate reductase, more preferably, lipophilic inhibitors of dihydrofolate reductase which are suitable for anti-parasitic therapies, especially anti-*Pneumocystis carinii* (Pc) and anti-*Tozoplasma gondii* (Tg) therapy, particularly in immunocompromised patients such as HIV-positive subjects.

The invention also provides pharmaceutical compositions comprising a compound of the above Formula I suitable together with a pharmaceutically acceptable carrier.

Other aspects of the of the invention are discussed infra.

DETAILED DESCRIPTION OF THE INVENTION

As discussed above, we now provide new methods for the synthesis of optionally substituted diarylmethane compounds of the general formula, Ar—R, where Ar is a carbocyclic aryl or a heteroaryl group and R is optionally substituted aralkyl, optionally substituted arylmethyl or optionally substituted heteroarylmethyl.

In methods of the invention, formation of the aryl-aralkyl bond is mediated by a metal complex. Metal complexes, particularly nickel, palladium and platinum complexes, capable of oxidative addition across aryl halide bond and reductive elimination of a diarylmethane compound, Ar—R, from a metal(aryl)(aralkyl) intermediate are suitable catalysts for the methods of the invention.

The invention features a method of forming a compound of the formula, Ar—R, the method comprising the step of contacting an aryl halide or aryl substrate with a nucleophilic leaving group, organozinc species capable of transmetalation, and a metal complex capable of effecting the coupling of an aryl substrate and an organozinc species to synthesize a compound of the formula Ar—R where Ar is an aryl or heteroaryl group and R is an aralkyl group or (heteroaryl)methyl group.

The present invention features a method of forming a compound of the general formula, Ar—R, the method comprising the step of contacting a mixture of aryl halide, ArX, and an organozinc species, RZnY, in the presence of at least a catalytic amount of a palladium complex under conditions conducive to the formation of an Ar—R bond, wherein:

Ar is optionally substituted phenyl, optionally substituted 1-naphthyl, optionally substituted 2-naphthyl, or optionally substituted heteroaryl having from 5 to about 18 ring atoms, 1 to about 3 rings and 1 to about 4 ring heteroatoms selected from N, O or S;

R is optionally substituted aralkyl;

X is Cl, Br, I, arylsulfonate, alkylsulfonate or triflate; and

Y is F, Cl, Br, I, arylsulfonate, alkylsulfonate or triflate.

Preferred methods of the invention for forming Ar—R compounds include contacting the aryl halide, organozinc species and palladium complex in an inert solvent. Preferred inert solvents suitable for use in the present invention are not particularly limited. Typically, inert solvents do not react irreversibly with the aryl halide, organozinc or palladium complex. Reversible coordination of one or more inert solvent molecules to zinc or palladium metal center of the organozinc species or palladium complex is acceptable. Preferred inert solvents for use in the methods of the invention are selected from hydrocarbons, aromatic hydrocarbons, chlorinated hydrocarbons, or oxygenated hydrocarbons. More preferred solvents include ethers including cyclic ethers, nitriles, N,N-dialkylformamides, N,N-dialkylacetamides, and optionally substituted benzenes having 0-3 alkyl groups and the like. Particularly preferred solvents include N,N-dimethylformamide, N,N-dimethylacetamide, acetonitrile, propylene carbonate, vinylene carbonate, diethyl ether, tert-butylmethylether, tetrahydrofuran, dioxane, dioxolane, benzene, toluene, ethylbenzene or xylenes. Most preferred inert solvents include tetrahydrofuran, dioxane, acetonitrile, toluene, ethyl benzenes and xylenes.

The mixture of aryl halide, organozinc species and palladium complex is typically mixed in an inert solvent so that the aryl halide, ArX, concentration is about 0.01 M to about 2 M. More preferably, the aryl halide concentration is greater than about 0.025 M, 0.05 M, 0.1 M or 0.2 M and the aryl halide concentration is less than about 2 M, 1.75 M, 1.5 M, 1.25 M, or 1 M. Particularly preferred are mixtures having the aryl halide concentration between about 0.1 M and about 1 M.

The aryl halide, organozinc species and palladium complex may be suitably contacted at or above 0° C., e.g., at a temperature of between about 0° C. and about 150° C. The temperature of the mixture can be substantially stable during the course of the reaction mixture or the temperature may be varied, e.g., initial contacting of the aryl halide, organozinc and palladium catalyst can be effected at a lower temperature and after complete mixing of the components, the temperature is increased. Preferably, the temperature of the reaction mixture is between about 15° C. and about 130° C., more preferably the initial contacting is carried out at a temperature between about 15° C. and about 130° C. and the reaction mixture is heated to a temperature of at least about 30° C. or 40° C. and the temperature does not exceed about 150° C., 140° C., 130° C., 120° C., 110° C., 100° C. or 90° C. In particularly preferred methods of the invention the reaction mixture comprising aryl halide, organozinc species and palladium complex is heated to a temperature at which the reaction mixture refluxes.

Typical reaction times can vary rather widely depending on reagents and reaction conditions. For example, the formation of Ar—R compound is complete within about 1 minute and about 1 week of contacting the aryl halide, organozinc species and palladium complex. Typically, the formation of Ar—R compound is complete in less than about 72 hours, 48 hours, 36 hours, 24 hours, 20 hours, 16 hours, 12 hours, 10 hours, 8 hours, 6 hours, or 4 hours and the formation of Ar—R compound generally takes at least 1 minute, 5 minutes or about 10 minutes. Preferably, the formation of Ar—R compound is complete in about 5 minutes to about 16 hours or more preferably 10 minutes to about 4 hours.

Suitably a reaction proceeds to substantial completion, e.g., at least 50 mole % of the aryl halide is converted into Ar—R compound. More preferably at least 55 mole %, 60 mole %, 65 mole %, 70 mole %, 75 mole %, 80 mole %, 85 mole %, 90 mole %, 95 mole % or 99 mole % of the aryl halide is converted into Ar—R compound. In preferred embodiments at least about 75 mole %, about 90 mole % or about 95 mole % of aryl halide is converted into Ar—R compound.

Either the aryl halide or the organozinc species can be the limiting reagent for the formation of Ar—R compound by the methods of the present invention. Preferably, the aryl halide is the limiting reagent. However, in certain embodiments it may be desirable for the organozinc species to be the limiting reagent. In preferred methods, the molar ratio of the aryl halide component to the organozinc species is between about 10:1 and about 1:10, more preferably the molar ratio is between about 1:1 and 1:10, between about 1:1.5 and about 1:5, or between about 1:1.5 and about 1:3. Particularly preferred molar ratios of the aryl halide and organozinc species are 1:1.5, 1:2, 1:2.5, 1:3, 1:3.5, 1:4 and 1:5.

Catalysts suitable for use in formation of Ar—R compounds from an aryl halide and an organozinc species are not particularly limited. Typically, catalysts include any catalyst suitable for Suzuki biaryl coupling or Buchwald aryl halide-amine coupling reactions such as inorganic or organometalic complexes of nickel, palladium or platinum, more preferred catalysts are palladium catalysts where palladium is in the palladium(0) or palladium (II) oxidation state.

While not being bound by theory, a typical catalyst facilitates formation of the Ar—R product by the catalytic cycle depicted in Scheme 1 below wherein an aryl halide added across a reduced metal center, $L_nM$, by oxidative addition to form a metal(aryl)(halide) complex, $L_nM(aryl)$(halide). Transalkylation of the metal halide bond by the organozinc species, RZnY, results in the formation of a metal (aryl)(alkyl) complex and a zinc salt byproduct. Reductive elimination of the product Ar—R through formation of the Ar—R bond regenerates the reduced metal center, $L_nM$, to reinitiate the catalytic cycle.

Scheme 1:

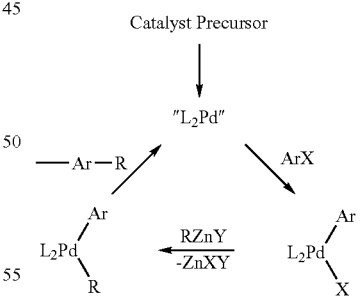

In general, ancillary ligands, $L_n$, are not particularly limited. In practice, typical ancillary ligands are frequently phosphines, particularly chelating bis(phosphines), and amines, particularly bipyridines. Particularly preferred ancillary ligands are chelating bis(phosphines) Preferred catalysts include palladium phosphine complexes which are either preformed or formed in situ from a palladium source and a phosphine. Preferred preformed catalysts include palladium (II) complexes $L_2PdCl_2$ and $L_2PdBr_2$ and palladium (0) complexes $L_2Pd(olefin)$ where $L_2$ is typically a chelating bis(phosphine) and olefin is an olefin which can coordinate to palladium such as ethylene, terminal and internal alkenes, styrene, stilbene, di(alkyl)fumerate, norbornene, norbornadiene and the like. Preferred in situ catalysts "$L_2Pd$" are generated from a chelating bisphosphine ($L_2$) and a palladium(0) source such as $Pd_2$(dibenzylideneacetone)$_3$ and solvates thereof, palladium(0) phosphine complexes such as tetrakis(triphenylphosphine)palladium (0), bis(tricyclohexylphosphine)palladium(0) and other homoleptic palladium(0) phosphine complexes, and Pd(olefin)$_n$ complexes selected from Pd(ethylene)$_3$, Pd(norbornadiene)$_2$, Pd(1,5-cyclooctadiene)$_2$ and other stable isolable palladium olefin complexes. Other preferred in situ catalysts "$L_2Pd$" are generated from a chelating diphosphine ($L_2$), a palladium(II) source such as palladium acetate and a reductant such as excess organozinc species.

In other preferred embodiments, the palladium catalyst is a $L_2Pd$ complex which may comprise additional ligands bound to palladium, and L is phosphite or phosphite or $L_2$ taken in combination is chelating ligand selected from bis(phosphine), bis(phosphite), phosphine-phosphite or 2,2'-bipyridine derivative. More preferred palladium catalysts include those wherein $L_2$ is optionally substituted 1,1'-bis(diarylphosphino)-ferrocene, optionally substituted 2,2'-bis(diarylphosphino)-binaphthyl, optionally substituted 2,2'-bis(diarylphosphino)-biphenyl, optionally substituted α,ω-bis(diarylphosphino)-$C_{1-6}$alkylene, optionally substituted 1,2-bis(di$C_{1-8}$alkylphosphino)benzene, or 2,2'-bis(diarylphosphino)-diarylether.

In particularly preferred palladium catalysts suitable for use in the present invention include those wherein the ancillary ligand, $L_2$, is 1,1'-bis(diarylphosphino)-ferrocene, 2,2'-bis(diarylphosphino)-binaphthyl, or 2,2'-bis(diarylphosphino)-diphenylether; and aryl is phenyl, 2-tolyl, 3-tolyl, or 4-tolyl.

Particularly preferred palladium catalysts include $L_2PdBr_2$, and mixtures of Pd(olefin)$_n$ and $L_2$, a chelating bis(phosphine), wherein olefin is selected from dibenzylidene acetone, norbornadiene, 1,5-cyclooctadiene, and ethylene such that 3 or 4 C=C bonds are coordinated to Pd; and $L_2$ is selected from 1,1'-bis(diarylphosphino)-ferrocene, 2,2'-bis(diarylphosphino)-binaphthyl, or 2,2'-bis(diarylphosphino)-diphenylether.

Preferred in situ catalysts prepared from a mixture of Pd(olefin)$_n$ and a chelating bis(phosphine) are generated by mixing the Pd(olefin)$_n$ and chelating bis(phosphine) at a molar ratio between about 1:1 and about 1:3 or more preferably between about 1:1 and about 1:1.5.

In preferred methods of the invention, the initial concentration of palladium is less than the initial concentration of the aryl halide component, e.g., the palladium complex is present in a catalytic or substoichiometric quantity. Typically, the palladium catalyst is less than about 25 mole %, 20 mole %, 15 mole %, 10 mole %, 5 mole %, 4 mole %, 2.5 mole %, 2 mole % or 1 mole % relative to the aryl halide (Ar—X) component. Particularly preferred palladium catalyst loadings are less than about 5 mole %, 2 mole % and 1 mole % relative to aryl halide.

In preferred embodiments of the present invention, organozinc compounds suitable for the palladium catalyzed cross-coupling reactions of the present invention include organozinc compounds of Formula II:

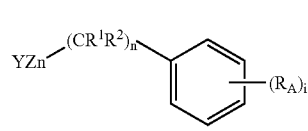

II wherein

Y is as defined in claim 1;

$R^1$ and $R^2$ are independently selected at each occurrence of $R^1$ and $R^2$ from the group consisting of hydrogen, $C_{1-6}$alkyl, $C_{2-6}$alkenyl, $C_{2-6}$alkynyl, or $C_{3-8}$cycloalkyl;

$R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, $C_{1-4}$fluoroalkyl, amino, mono and di($C_{1-6}$alkyl)amino, nitrile, optionally substituted aryloxy, optionally substituted heteroaryloxy, $C_{1-6}$alkylthio, optionally substituted arylthio, optionally substituted heteroarylthio, optionally substituted aryl acetoxy or optionally substituted heteroaryl acetoxy; or two $R_A$ groups on adjacent ring atoms taken in combination form a second ring optionally comprising zero, one or two hetero ring atoms;

n is an integer from 1 to about 4; and i is an integer from 0 to 5.

Preferred organozinc compounds of Formula II which are suitable for use in the methods of the present invention include those of formula III:

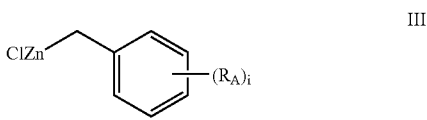

III wherein:

$R_A$ is independently selected at each occurrence of $R_A$ from the group consisting of hydrogen, chloro, fluoro, $C_{1-4}$alkyl, $C_{1-4}$alkoxy, and $C_{1-2}$fluoroalkyl;

i is an integer from 0 to about 3.

In preferred embodiments of the present invention, aryl halide compounds, ArX, suitable for the palladium catalyzed cross-coupling reactions of the present invention include aryl halide compounds of Formula IV:

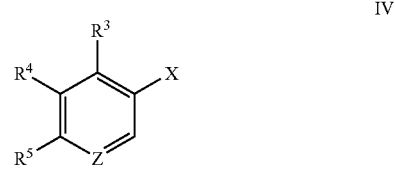

IV wherein:

$R^4$ and $R^5$ are independently selected from the group consisting of hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, amino, mono and di($C_{1-6}$alkyl)amino, and nitrile; or $R^4$ and $R^5$ taken in combination form a group of the formula:

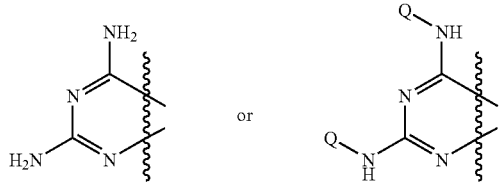

Q is independently selected at each occurrence of Q in Formula IV to be an amine protecting group stable to the cross-coupling reaction conditions of the methods of the present invention selected from alkanoyl, alkyloxycarbonyl, aryloxycarbonyl, benzyloxycarbonyl, silyl and the like.

X is I or Br; and

Z is N or $CR^3$;

$Z^1$ is N or CH; and $R^3$ is hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, $C_{1-6}$alkylthio, optionally substituted arylthio, or optionally substituted arylalkylthio.

Preferred aryl halide compounds of Formula IV which are suitable for use in the methods of the present invention include those of formula V:

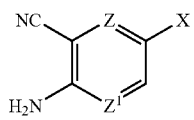

wherein:

X is Br or I;

Z is N or $CR^3$;

$Z^1$ is N or CH; and $R^3$ is hydrogen, methyl, ethyl, trifluoromethyl, methoxy, chloro, or fluoro.

Other preferred aryl halide compounds of Formula IV which are suitable for use in the methods of the present invention include those of formula VI:

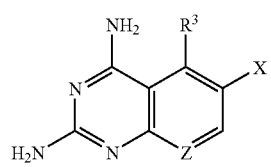

wherein:

X is Br or I;

Z is N or CH; and $R^3$ is hydrogen, methyl, ethyl, trifluoromethyl, methoxy, chloro, or fluoro.

Additionally preferred compounds according to Formula VI include those where the amino groups of the pyrimidine ring are masked with standard amino protecting groups.

In particularly preferred methods of the invention the Ar—R compound formed by cross-coupling is a compound according to Formula I:

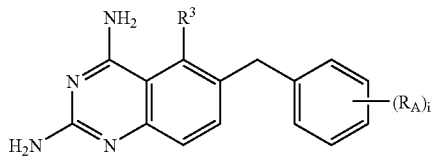

the method comprising the steps of contacting an aryl halide of the formula:

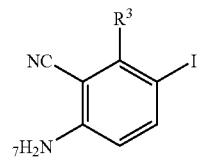

with at least one molar equivalent of a organozinc reagent, RZnY, and at least a catalytic amount of a palladium catalyst under conditions conducive to the formation of an C—C bond by a palladium mediated cross-coupling reaction;

contacting the product of the cross-coupling reaction with chloroformamidine hydrogen chloride salt under dry-fusion conditions conducive to formation of a compound according to Formula I, wherein $R_A$ is independently selected at each occurrence of $R_A$ from the group consisting of hydrogen, $C_{1-6}$alkyl, $C_{1-6}$alkoxy, chloro, fluoro, nitro, and trifluoromethyl; or two adjacent $R_A$ groups taken in combination form a group of the formula:

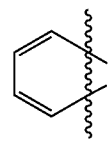

which may be optionally substituted;

$R^3$ is hydrogen, methyl, ethyl, chloro, fluoro, trifluoromethoxy, or methoxy; and Y is Cl, Br, I, or triflate.

The present invention also features compounds according to Formula I:

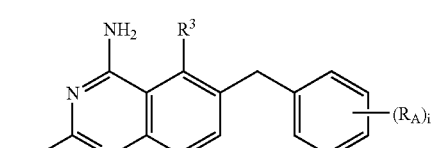

wherein:

$R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, $C_{1-4}$fluoroalkyl, amino, mono and di($C_{1-6}$alkyl) amino, nitrile, optionally substituted aryloxy, optionally substituted heteroaryloxy, $C_{1-6}$alkylthio, optionally substituted arylthio, optionally substituted heteroarylthio, optionally substituted aryl acetoxy or optionally substituted heteroaryl acetoxy; or two adjacent $R_A$ groups taken in combination form a group of the formula:

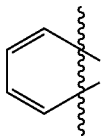

which may be optionally substituted;

$R^3$ is hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, $C_{1-6}$alkylthio, optionally substituted arylthio, or optionally substituted arylalkylthio; and i is an integer from 0 to about 5.

Preferred compounds of Formula I are lipophilic inhibitor of dihydrofolate reductase which are suitable for use in AIDS therapy. More preferred compounds of Formula I exhibit anti-parasitic activity against *Pneumocystis carinii* (Pc) and *Tozoplasma gondii* (Tg).

Other preferred compounds of Formula I include those wherein $R_A$ is independently selected at each occurrence from the group consisting of hydrogen, fluoro, chloro, methoxy, methyl, and trifluoromethyl; or two adjacent $R_A$ groups taken in combination form a group of the formula:

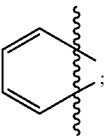

$R^3$ is hydrogen, methyl, ethyl, chloro, fluoro, hydroxy, amino, trifluoromethoxy, or methoxy. More preferably, $R^3$ is hydrogen, methyl, chloro or fluoro; and i is an integer from 0 to about 3.

Particularly preferred compounds of Formula I include those substituted 6-Benzyl-quinazoline-2,4-diamine compounds according to Formula I-A:

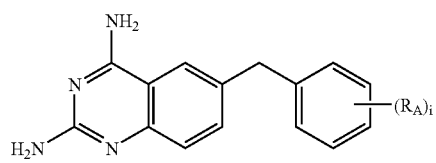

wherein $R_A$ is independently selected at each occurrence from the group consisting of hydrogen, fluoro, chloro, methoxy, methyl, and trifluoromethyl; or two adjacent $R_A$ groups taken in combination form a group of the formula:

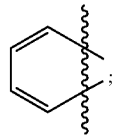

i is an integer from 0 to about 3.

Suitable halogen substituent groups or halide groups of compounds of the invention, including compounds of Formula II, III, IV, V, and VI as defined above, include F, Cl, Br and I. Alkyl groups of compounds of the invention preferably have from 1 to about 12 carbon atoms, more preferably 1 to about 8 carbon atoms, still more preferably 1 to about 6 carbon atoms. As used herein, the term alkyl unless otherwise modified refers to both cyclic and noncyclic groups, although of course cyclic groups will comprise at least three carbon ring members. Straight or branched chain noncyclic alkyl groups are generally more preferred than cyclic groups, particularly branched chain groups such as isopropyl and t-butyl. Preferred alkenyl groups of compounds of the invention have one or more unsaturated linkages and from 2 to about 12 carbon atoms, more preferably 2 to about 8 carbon atoms, still more preferably 2 to about 6 carbon atoms. The term alkenyl as used herein refer to both cyclic and noncyclic groups, although straight or branched noncyclic groups are generally more preferred, particularly branched chain groups. Preferred alkoxy groups of compounds of the invention include groups having one or more oxygen linkages and from 1 to about 12 carbon atoms, more preferably from 1 to about 8 carbon atoms, and still more preferably 1 to about 6 carbon atoms. Preferred thioalkyl groups of compounds of the invention include those groups having one or more thioether linkages and from 1 to about 12 carbon atoms, more preferably from 1 to about 8 carbon atoms, and still more preferably 1 to about 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms. Substituted and unsubstituted mono and dialkylamino groups are particularly preferred, especially where each alkyl chain of the group has from 1 to about 6 carbon atoms. Preferred alkylsulfoxide of compounds of the invention have one or more sulfoxide groups, more typically one sulfoxide group, and from 1 to about 12 carbon atoms, more preferably 1 to about 8 carbon atoms, still more preferably 1 to about 6 carbon atoms. Preferred sulfonoalkyl groups of compounds of the invention have one or more sulfono ($SO_2$) groups, more typically one or two sulfono groups, and from 1 to about 12 carbon atoms, more preferably 1 to about 8 carbon atoms, still more preferably 1 to about 6 carbon atoms. Preferred alkanoyl groups of compounds of the invention include groups having one or more carbonyl groups, more typically one or two carbonyl groups, and from 1 to about 12 carbon atoms, more preferably 1 to about 8 carbon atoms, still more preferably 1 to about 6 carbon atoms. Preferred alkylcarboxyamino groups include those groups of the formula —NHCOOR where R is substituted or unsubstituted alkyl having from 1 to about 10 carbon atoms, more preferably 1 to about 6 carbon atoms. Suitable heteroaromatic groups of compounds of the invention contain one or more N, O or S atoms and include, e.g., quinolinyl, pyridyl, pyrazinyl, indolyl, carbazoyl, furyl, pyrrolyl, thienyl, thiazolyl, aminothioazolyl such as 2-aminothiazolyl, pyrazolyl, oxazolyl, imidazolyl, indolyl, benzofuranyl, benzothiazolyl and pyridonal including 2-pyridonals and 4-pyridonals, particularly pyridonal substituted at one or more ring positions by moieties such as hydroxy, alkanoyl such as acetate, alkylaminocarbonyl having from 1 to about 8 carbon atoms and alkoxycarbonyl having from 1 to about 8 carbon atoms. Suitable heteroalicyclic groups of compounds contain one or more N, O or S atoms and include, e.g., aziridinyl, azetidinyl, tetrahydrofuranyl, tetrahydropyranyl, pyrrolidinyl, 1,2,3,6-tetrahydropyridinyl, piperazinyl, piperidinyl, morpholinyl and thiomorpholinyl.

Substituted moieties of compounds of the invention, including substituted $R_A$, $R^1$, $R^2$, and $R^3$ groups, may be "optionally substituted," that is groups may be substituted at one or more available positions by one or more suitable groups such as, e.g., halogen such as fluoro, chloro, bromo and iodo; cyano; hydroxyl; nitro; alkyl groups including those groups having 1 to about 12 carbon atoms or from 1 to about 6 carbon atoms, preferably noncyclic alkyl groups including branched chain groups such as isopropyl and t-butyl; alkenyl and alkynyl groups including groups having one or more unsaturated linkages and from 2 to about 12 carbon or from 2 to about 6 carbon atoms; alkylthio groups including those moieties having one or more thioether linkages and from 1 to about 12 carbon atoms or from 1 to about 6 carbon atoms; and, in at least preferred aspects of the invention, alkoxy groups having those having one or more oxygen linkages and from 1 to about 12 carbon atoms or 1 to about 6 carbon atoms; and aminoalkyl groups such as groups having one or more N atoms (which can be present as primary, secondary and/or tertiary N groups) and from 1 to about 12 carbon atoms or from 1 to about 6 carbon atoms.

Particularly preferred substituent groups of compounds of the invention, including compounds of Formulae I, I-A, II, III, IV, V and VI, include nitrogen containing groups including aminoalkyl, alkylcarboxyamino and nitrogen-containing heteroaromatic and heteroalicyclic groups. Preferred nitrogen-containing cyclic groups include those moieties that have one or two heteroatoms, e.g. one or two N, O, or S atoms. Preferably benzyl groups of organozinc species of Formula II and III and cross-coupled products prepared therefrom are substituted with one, two or three groups selected from halogen, alkyl groups having 1 to about 6 carbon atoms, alkenyl groups having 2 to about 6 carbon atoms, alkynyl groups having 2 to about 6 carbon atoms, alkoxy groups having 1 to about 6 carbon atoms, trifluoromethyl, amino or a saturated, partially unsaturated or unsaturated ring is fused the benzyl ring.

The present invention provides a straightforward and versatile approach that can lend itself to the synthesis of a rich library of previously unknown biologically active DHFR inhibitors in which a substituted aryl group is linked directly to the 2,4-diamino heterocyclic moiety via a $CH_2$ bridge. The present invention also provides a new class of biologically active compounds according to formula I which are active DHFR inhibitors.

The present invention provides methods of making biologically active DHFR inhibitors having a methylene linkage between two aromatic groups wherein the methylene linkage is formed by a cross coupling reaction between an aromatic halide and an organozinc complex catalyzed by a group 10 metal such as nickel or palladium.

Organozinc reagents in combination with nickel or palladium reagents are extremely useful in the synthesis of complex molecules containing multiple functional groups, such as natural products. Of particular note is that preferred reactions of the invention can require only a catalytic amount of palladium, and that, in contrast to the Heck reaction, the saturated carbon-carbon is generated directly, without the need to first reduce a double or triple bond. A large number of organozinc reagents are available commercially as standardized solutions in THF, or can readily be prepared from organic halides and a highly reactive grade of metallic zinc ("Rieke zinc"), (Zhu, L.; Wehmeyer, R. M.; Rieke, R. D. J. Org. Chem. 1991; 56, 1445-1453) which is likewise commercially available.

In non-limiting examples of the methods of the present invention, a novel and remarkably straightforward method of synthesis of compounds according to Formula I, e.g., 6-benzyl-quinazoline-2,4-diamine and derivatives thereof, are provided. A key step in the synthesis of these compounds is the previously unknown palladium-catalyzed cross-coupling reaction between an 2-amino-5-iodobenzonitrile and an arylmethylzinc halide reagent. The methods of the invention typically can be effected without protection of amino groups. However, in certain applications protection of some or all of the functional groups present in the substrate may be advantageous.

Ring closure of the resulting cross-coupled aminonitriles by heating them with chloroformamidine hydrochloride under previously described dry-fusion conditions yielded certain compounds according to Formula I. See for example Rosowsky, A.; Mota, C. E.; Wright, J. E.; Freisheim, J. H.; Heusner, J. J.; McCormack, J. J.; Queener, S. F. J. Med Chem. 1993; 36, 3103-3112. For other reaction conditions under which aminonitriles can be condensed with chloroformamidine hydrochloride or cyanamide/pyridinium chloride, its synthetic equivalent, to obtain various types of di- and tricyclic 2,4-diaminopyrimidine derivatives, see: (a) Rosowsky A.; Modest, E. J. J. Org. Chem. 1966; 31, 2607-2613. (b) Rosowsky, A.; Marini, J. L.; Nadel, M.; Modest, E. J. J. Med. Chem. 1970; 13, 882-886. (c) Elslager E. F.; Jacob, P.; Werbel, L. M. J. Heterocycl. Chem. 1972; 9, 775-782. (d) Elslager, E. F.; Bird, O. D.; Clarke, J.; Perricone, S. C.; Worth, S. F. J. Med Chem. 1972; 15, 1138-1146; (e) Rosowsky, A.; Chen, K. K. N.; Lin M. J. Med Chem. 1973; 16, 191-194; (f) Ashton, W. T.; Hynes, J. B. J. Med Chem. 1973; 16, 1233-1237. (g) Harris, N. V.; Smith, C.; Bowden, K. J. Med Chem. 1990; 33, 434-444.

One general synthetic procedure for the methods of the present invention is depicted in Scheme 2 below. Iodination of 2-aminobenzonitrile with iodine monochloride in glacial acetic acid (AcOH) at room temperature occurred regioselectively at the position para to the amino group to give 2-amino-5-iodobenzonitrile (9) in 65% yield as reported by others (Harris, N. V.; Smith, C.; Bowden, K. Eur. J. Med Chem. 1992; 27, 7-18). A catalytic amount (0.1 mmol) of commercially available [1,1'-bis(diphenylphosphino)ferrocene]-dichloropalladium(II)'$CH_2Cl_2$ [(dppf)PdCl$_2$—CH$_2$Cl$_2$] (Hayashi, T.; Konishi, M.; Kobori, Y.; Kumada, M.; Higuchi, T.; Hirotsu, K. J. Am Chem. Soc. 1984, 106, 158-163) was added to a THF solution of the organozinc halide (5 mmol) resulting in the formation of a solution having a deep yellow color after a few minutes. After complete addition of (dppf)PdCl$_2$ to the reaction mixture, a solution of aryl halide 9 (2 mmol) in THF was added to the reaction mixture and the mixture was then heated at reflux for 30 min. The cross-coupling reaction was complete to thin layer chromatography (TLC). The intermediate amino nitrile 10 formed by the cross-coupling reaction were purified by column chromatography on silica gel, and their identity and purity were established from their $^1$H NMR spectra, which contained the expected singlet at approximately δ 3.8, along with OMe, NH$_2$, and aromatic proton peaks consistent with assigned structures (data provided below).

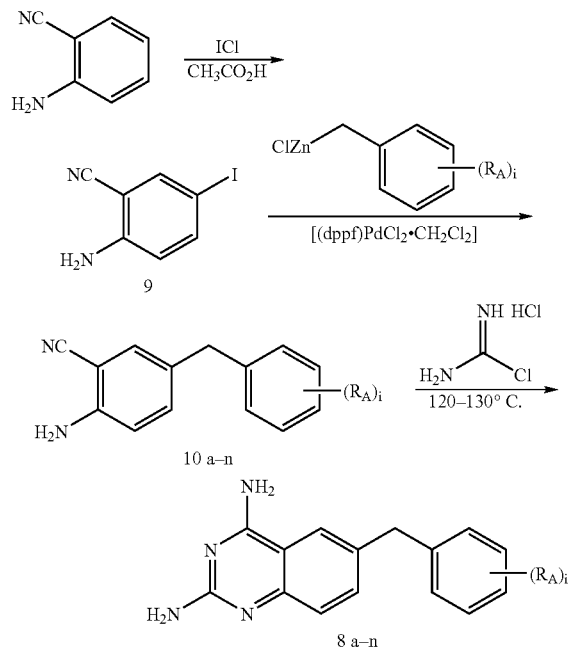

Ring closure of intermediate 10 to form compound 8 according to Formula I was performed by heating a finely ground mixture of intermediate 10 and chloroformamidine hydrochloride in an open pear-shaped flask, in the absence of a solvent, at 120-130° C. for 20 minutes. The resultant melt is allowed to congeal at room temperature, and is taken up in methanol (MeOH). Addition of chloroform (CHCl$_3$) caused precipitation of by-products arising from thermally induced self-condensation/polymerization of chloroformamidine hydrochloride. The MeOH—CHCl$_3$ filtrate at this stage contains the hydrochloride salt of the diaminoquinazoline, as well as the salt of a second product believed to be a non-cyclized amidinonitrile intermediate (Rosowsky, A., et al.; *J. Med Chem.* 1993; 36, 3103-3112).

In certain embodiments, further heating of the reaction mixture while applying a vacuum (P<100 mTorr) may be required to drive the ring closure reaction to completion. The examples provided in the present invention are illustrative and one of ordinary skill in the synthetic arts will be able to readily modify the reaction conditions provided herein as necessary for a desired compound.

$^1$H NMR spectra of 8a-n showed the expected signals for a 2,4-diamino-6-arylmethyl-quinazoline, among which were a singlet at approximately δ 3.9 for H-5 and doublets at approximately δ 7.1 (J=8.4-8.8 Hz) and δ 7.3 (J=8.4-8.8 Hz) for H-8 and H-7, respectively. Signals for the other aromatic protons had chemical shifts and coupling constants in agreement with the nature and location of the substituents on the benzyl ring. The identity of each final product was also confirmed by microchemical analysis and mass spectrometry.

Many other 6-benzyl-2,4-diaminoquinzoline inhibitors of DHFR with substitution on the 6-benzyl group or with substitution on the quinzoline ring system can be prepared by the methods of the invention used to prepare the compounds of Examples 1-14 described herein. Thus, using commercially available benzylic halide or arylmethylzinc halide starting materials, the following compounds can be made from 9 by Pd-catalyzed cross-coupling followed by heating of the product with chloroformamidine hydrochloride under solvent-free dry-fusion conditions or in the presence of an inert diluent (e.g. diphenyl ether or diphenylsulfone), or by heating the product with a mixture of cyanamide and pyridine hydrochloride: 8 [R=2',4'-Cl$_2$, 2',6'-Cl$_2$, 3',5'-Cl$_2$, 3'-F, 4'-F, 2',3'-F$_2$, 2',4'-F$_2$, 2', 5'-F$_2$, 2',6'-F, 3',4'-F, 3',5'-F$_2$, 2'-CF$_3$, 3'-CF$_3$, 4'-CF$_3$, 3'-CF$_3$O, 4'-CF$_3$O, 2',3'-(OMe)$_2$, 2',4'-(OMe)$_2$, 2',6'-(OMe)$_2$, 2'-EtO, 4'-EtO, 4'-CN, 4'-CO$_2$Et, 2'-Me, 3'-Me, 4'-Me, 2',5'-Me$_2$, 3',4'-Me$_2$, 1',2'-(CH=CH)$_2$]. Where the benzylic halide is not commercially available it can easily be synthesized from the corresponding alcohol.

Substituted 2-amino-5-iodo-benzonitriles are also suitable for use in the present invention. For example, 3-substituted benzonitriles having alkyl, alkoxy or chloro groups are preferred benzonitriles for use in the methods of the present invention, see Scheme 3. In for benzonitriles having a 3-chloro substituent, the oxidative addition of the arylhalide bond is chemo-selective by virtue of the greater ease of addition across aryl bromide or aryl iodide bonds.

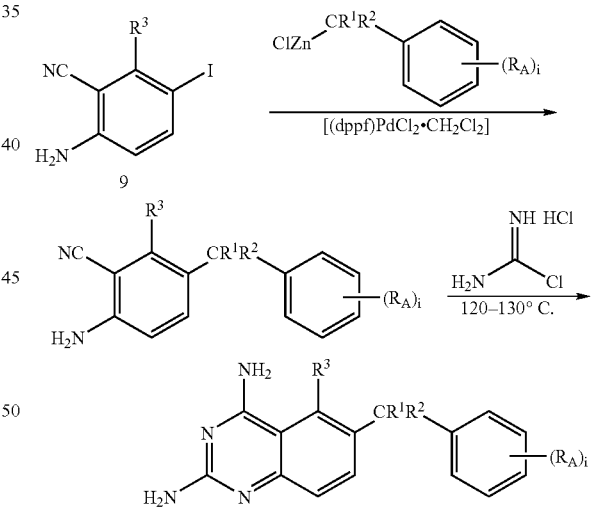

In another aspect of the present invention (Scheme 4), the palladium-catalyzed cross-coupling reaction can also be applied to pre-formed 2,4-diamino-6-iodoquinazoline substrates (11), which can be readily obtained from 9 and chloroformamidine hydrochloride. Protection of the 2- and 4-amino groups with standard amino blocking groups, such as N-pivaloyl groups, solubilized the diaminoquinazoline in organic solvents such as THF. The amino protected substrates are compatible with the cross-coupling procedures of the invention and subsequent deprotection of the blocked amino groups is facile.

Scheme 4.

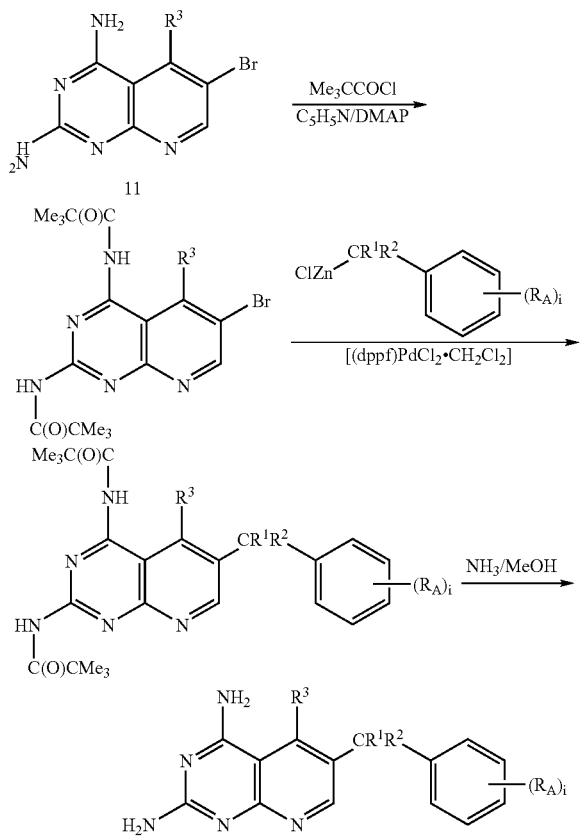

In additional, 2,4-diamino-6-arylmethylpyrido[2,3-d]pyrimidines (Scheme 4) and 2,4-diamino-6-arylmethylpteridines may be prepared from known starting materials such as optionally substituted 2,4-diamino-6-bromopyrido[2,3-d]pyrimidine (12) (Gangjee, A; Devraj, R.; Lin, F.-T. *J. Heterocycl. Chem.* 1991; 28, 1747-1750) and optionally substituted 2-amino-5-bromopyrazine-3-carbonitrile (Taylor, E. C.; Ray, P. S. *J. Org. Chem.* 1987; 52, 3997-4000) to prepare diverse libraries of biologically active DHFR inhibitors.

Thus the compounds of the present invention, particularly compounds of Formula I and I-A are useful as pharmaceuticals for the treatment of mammals, including humans, particularly for the treatment of mammals suffering from or susceptible to an immunodeficiency disorder, such as a mammal that is HIV positive, particularly a human suffering from or susceptible to AIDS. Other immuno-comprised subjects also will benefit from the therapies of the invention, such as a subject suffering from an autoimmune disorder and the like.

Compounds of the invention are particularly useful to combat parasitic infections which are known to inflict HIV-positive or patients suffering from or susceptible to AIDS. Thus, the invention provides a method for the treatment of a subject that is suffering from AIDS, or is otherwise immuno-compromised, the method comprising administration of an effective amount of one or more compounds of the invention in a pharmaceutically useful form, once or several times a day or other appropriate schedule, orally, rectally, parenterally (particularly intravenously), topically, etc.

For such treatment, the compounds of the invention are administered in effective amounts and in appropriate dosage form ultimately at the discretion of the medical or veterinary practitioner. For example, as known to those skilled in the art, the amount of compounds of the invention required to be pharmaceutically effective will vary with a number of factors such as the mammal's weight, age and general health, the efficacy of the particular compound and formulation, route of administration, nature and extent of the condition being treated, and the effect desired. The total daily dose may be given as a single dose, multiple doses, or intravenously for a selected period. Efficacy and suitable dosage of a particular compound can be determined by known methods. More particularly, for treatment of a tumor in a mammal such as a human, particularly when using more potent compounds of the invention, a suitable effective dose of the compound of the invention will be in the range of 0.1 to 100 milligrams per kilogram body weight of recipient per day, preferably in the range of 1 to 10 milligrams per kilogram body weight of recipient per day. The desired dose is suitably administered once daily, or as several sub-doses, e.g. 2 to 4 sub-doses administered at appropriate intervals through the day, or other appropriate schedule. Such sub-doses may be administered as unit dosage forms, e.g., containing from 0.2 to 200 milligrams of compound(s) of the invention per unit dosage, preferably from 2 to 20 milligrams per unit dosage.

The compounds of the present invention may be suitably administered to a subject as a pharmaceutically acceptable salt. Such salts can be prepared in a number of ways. For example, where the compound comprises a basic group such as an amino group, salts can be formed from an organic or inorganic acid, e.g. hydrochloride, sulfate, hemisulfate, phosphate, nitrate, acetate, oxalate, citrate, maleate, etc.

The therapeutic compound(s) may be administered alone, or as part of a pharmaceutical composition, comprising at least one compound of the invention together with one or more acceptable carriers thereof and optionally other therapeutic ingredients, e.g., other AIDS agents such as a cocktail of therapeutic agents. Possible other therapeutic agents included in such a cocktail include, e.g., AZT, 3TC, and the like as well as other anti-parasitic or anti-biotic agents. The carrier(s) must be "acceptable" in the sense of being compatible with the other ingredients of the formulation and not deleterious to the recipient thereof.

The compositions include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well known in the art of pharmacy.

Such methods include the step of bringing into association the to be administered ingredients with the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for topical administration to the skin may be presented as ointments, creams, gels and pastes comprising one or more compounds of the present invention and a pharmaceutically acceptable carrier. A suitable topical delivery system is a transdermal patch containing the ingredient to be administered.

Compositions suitable for rectal administration may be presented as a suppository with a suitable base comprising, for example, cocoa butter or a salicylate.

Compositions suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above the formulations of this invention may include other agents conventional in the art having regard to the type of formulation in question, for example, those suitable for oral administration may include flavoring agents.

The following non-limiting examples are illustrative of the invention. All documents mentioned herein are incorporated herein by reference in their entirety.

General Comments

In the following examples, IR spectra were obtained on a Perkin-Elmer Model 781 double-beam recording spectrophotometer. Only peaks with wave numbers greater than 1400 cm$^{-1}$ are reported. $^1$H NMR spectra were recorded at 200 MHz on a Varian VX200 instrument or at 400 MHz on a Varian VX400 instrument. TLC analyses were on Whatman MK6F silica gel plates with UV illumination at 254 nm. Column chromatography was on Baker 7024 flash silica gel (40 µM particle size). Melting points were measured in Pyrex capillary tubes in a Mel-Temp 'Electrothermal' apparatus (Fisher Scientific, Pittsburgh, Pa.). and are not corrected. Mass spectra in the electron-impact (EI) or fast-atom bombardment (FAB) mode were obtained by staff of the Dana-Farber Cancer Institute Molecular Biology Core Facility. The palladium catalyst [1,1'-bis(diphenylphosphino)ferrocene] dichloropalladium(II)-CH$_2$Cl$_2$ and other chemicals, including Rieke-grade active zinc as a suspension in dry THF, were purchased from Aldrich, Milwaukee, Wis. Solutions of 3,4-dichlorobenzylzinc chloride, 2,5-dimethoxybenzylzinc chloride and 3,4,5-trimethoxybenzylzinc chloride in dry THF were prepared and used essentially as described in the literature for other organozinc reagents, (Zhu, L., et al.; *J. Org. Chem.* 1991; 56, 1445-1453) and were used immediately. Other organozinc reagents, supplied as 0.5 M solutions in THF in 'Sure-Seal' bottles, were purchased from Aldrich. The THF used in the zinc cross-coupling reactions was freshly distilled from Na benzophenone ketyl under a dry N$_2$ atmosphere. Chloroformamidine hydrochloride was prepared from cyanamide in ethereal HCl as described (Harris, N. V.; Smith, C.; Bowden, K. *Eur. J. Med Chem.* 1992; 27, 7-18). Elemental analyses were performed by Robertson Laboratories, Madison, N.J., and were within ±0.4% of theoretical values.

In the following examples, compound reference numerals are the same as specified in the above Schemes.

EXAMPLE 1

Synthesis of 2,4-Diamino-6-benzylquinazoline (Scheme 2; Compound 8a; (R$_A$)$_i$=hydrogen).

Step 1. A solution of iodine monochloride (16.7 g, 0.1 mol) in glacial AcOH (30 mL) as added dropwise over 15 min to a stirred solution of 2-aminobenzonitrile (11.8 g, 0.1 mol) in glacial AcOH (125 mL) at room temperature. The mixture was stirred for 3 h and then poured into H$_2$O (1000 mL). The resulting pinkish-brown solid was filtered, washed with H$_2$O, and dried in vacuo. Crystallization from cyclohexane-toluene (9:1) gave 2-amino-5-iodobenzonitrile (9) as translucent plates (14.9 g, 64%): mp 85-86° C. (lit. 85-86° C.); $^1$H NMR (CDCl$_3$) δ 7.60 (d, J=1.6 Hz, 1H, H-6), 7.57 (dd, J=9.2 Hz, 1.6 Hz, 1H, H-4), 6.53 (d, J=9.2 Hz, 1H, H-3), 4.45 (br s; 2H, NH$_2$). The product was used directly in the next reaction (Step 2).

Step 2. (DPPF)PdCl$_2$—CH$_2$Cl$_2$ (82 mg, 0.1 mmol) was added to 0.5 M benzylzinc bromide in dry THF (10 mL, calculated to contain 5 mmol), and the mixture was stirred at room temperature for 5 min under N$_2$. A solution of 9 (488 mg, 2 mmol) in dry THF (2 mL) was then added, and the reaction was heated under reflux and monitored by TLC (silica gel, 2:1 CH$_2$Cl$_2$-hexanes). After 30 min the reaction was quenched by addition of saturated aqueous NH$_4$Cl (10 mL) followed by saturated aqueous Na$_2$EDTA (10 mL), and stirring was continued for another 30 min. The brown mixture was extracted several times with CH$_2$Cl$_2$, and the combined extracts were washed with brine, dried over Na$_2$SO$_4$, and evaporated to dryness under reduced pressure. The residue was purified by chromatography on silica gel (2:1 CH$_2$Cl$_2$-hexanes) to obtain 2-amino-5-benzylbenzonitrile (10a) as a white powder (210 mg, 51%): mp 68–69° C.; $^1$H NMR (DMSO-d$_6$) δ 3.75 (s, 2H, CH$_2$), 5.85 (br s, 2H, NH$_2$), 6.70 (d, J=8 Hz, 1H, H-3), 7.13–7.26 (m, 7H, aromatic protons). The product was used directly in the next reaction (Step 3).

Step 3. A finely ground mixture of amino nitrile 10a (60 mg, 0.29 mmol) and chloroformamidine hydrochloride (132 mg, 1.16 mmol) was placed in a 10 mL pear-shaped flack, which was immersed in an oil bath and triturated continuously with a glass rod while being heated to 120° C. (internal temperature) under a gentle stream of N$_2$ as described (Rosowsky, A. et al.; *J. Med Chem*. 1993; 36, 3103-3112). After 20 min the reaction mixture was cooled to room temperature, the resulting glassy solid was dissolved in MeOH (0.75 mL), and the solution was diluted with CHCl$_3$ (12 mL) and chilled at 0° C. for 1 h. The solid precipitate was collected, washed with CHCl$_3$, and discarded. This solid consists mainly of by-products arising from the self-condensation of chloroformamidine, whereas the pooled filtrates contain the HCl salt of the desired product, along with a variable amount of the salt of what is presumed to an intermediate non-cyclized amidinonitrile of the type previously observed (Rosowsky, A. et al.; *J. Med Chem*. 1993; 36, 3103-3112). To ensure complete ring closure, excess i-Pr$_2$NH (0.5 mL) was added to the filtrate to neutralize the acid, the mixture was concentrated dryness on a rotary evaporator, and the solid residue was heated for 1.5 h at 70° C. under high vacuum (0.1 Torr). The crude product was then dissolved in boiling MeOH, and the solution treated with a little decolorizing carbon (Darco) and hot-filtered through a bed of Celite. When the filtrate became cool it was basified to pH 10 with ammonia, and the precipitate was collected. Recrystallization from MeOH—H$_2$O afforded 8a as a white crystalline solid (32 mg, 44%): mp 220–222° C.; MS: m/z 251.4, calcd 251.3 (M+1); IR (KBr) v 3340, 3170, 1620, 1570, 1510, 1450, 1400 cm$^{-1}$; $^1$H NMR (DMSO-d$_6$) δ 3.92 (s, 2H, CH$_2$), 5.84 (br s, 2H, 2-NH$_2$), 7.13 (d, J=8.6 Hz, 1H, H-8), 7.16–7.35 (m, ca. 6H, H-7 and other aromatic protons), 7.89 (s, 1H, H-5). In contrast to the majority of the other diaminoquinazolines described below, the hydrogens on the 4-NH$_2$ group apparently gave a signal at around δ 7.2 which was too broad to be observed. Anal. Calcd. for C$_{15}$H$_{15}$N$_4$-0.3H$_2$O: C, 70.46, H, 5.75, N, 22.16. Found: C, 70.20; H, 5.42; N, 22.28.

EXAMPLE 2

Synthesis of 2-Amino-5-(2'-chlorobenzyl)benzonitrile (Scheme 2; Compound 10b; (R$_A$)$_i$=2-Cl):

From 9 (488 mg, 2 mmol) and 2-chlorobenzylzinc chloride (0.5 Min THF, 10 mL, 5 mmol) by the same methods as 10a; white powder (272 mg, 62%), mp 79–80° C.; $^1$H NMR (CDCl$_3$) δ 3.96 (s, 2H, CH$_2$), 4.79 (br s, 2H, NH$_2$), 6.69 (d, J=8.8 Hz, 1H, H-3), 7.12–7.19 (m, 5H, aromatic protons), 7.20 (s, 1H, H-6).

2,4-Diamino-6-(2'-chlorobenzyl)quinazoline (Scheme 2; Compound 8b; (R$_A$)$_i$=2-Cl).

From 10b (180 mg, 0.74 mmol) and chloroformamidine hydrochloride (340 mg, 3 mmol) at130° C. (internal) for 30 min; white needles (79 mg, 38%): mp 220-222° C.; MS: m/z 285.2, calcd 285.8 (M+1); IR (KBr) v 3340, 3160, 1615, 1565, 1510, 1490, 1450, 1400 cm$^{-1}$; $^1$H NMR (DMSO-d$_6$) δ 4.02 (s, 2H, CH$_2$), 5.89 (br s, 2-NH$_2$), 7.12 (s, J=8.8 Hz, 1H, H-8), 7.19 (br s, 4-NH$_2$),7.25 (d, J=9.4 Hz, 2H, H-2' and H-6'), 7.32 (d, J=8.8 Hz, 1H, H-7), 7.34 (d, J=8.4 Hz, 2H, H-3' and H-5'), 7.88 (s, 1H, H-5). Anal. Calcd for C$_{15}$H$_{13}$N$_4$Cl0.2H$_2$O: C, 62.48; H, 4.58; N, 19.43; Cl, 12.29. Found: C, 62.52; H, 4.56; N, 19.63; Cl, 12.32.

EXAMPLE 3

Synthesis of 2-Amino-5-(3'-chlorobenzyl)benzonitrile (Scheme 2; Compound 10c; (R$_A$)$_i$=3-Cl):

From 9 (488 mg, 2 mmol) and 3-chlorobenzylzinc chloride (0.5 M in THF, 10 mL, 5 mmol) by the same method as 10a; white powder (269 mg, 55%): mp 84.5-85.5° C.; $^1$H NMR (CDCl$_3$) δ 3.82 (s, 2H, CH$_2$), 4.30 (br s, 2H, NH2), 7.02 (d, J=8.4 Hz, 1H, H-3), 7.12-7.22 (m, 5H, aromatic protons).

Synthesis of 2,4-Diamino-6-(3'-chlorobenzylquinazoline((Scheme 2; Compound 8c; (R$_A$)$_i$=3-Cl).

From 10c (107 mg, 0.44 mmol) and chloroformamidine hydrochloride (201 mg, 1.76 mmol) at 120° C. for 30 min; white needles (52 mg, 41%): mp 242-243° C.; MS: m/z 285.1, calcd 285.8 (M+1); IR (KBr) v 3440, 3200, 1620, 1565, 1510, 1470 cm$^{-1}$; $^1$H NMR (DMSO-d$_6$) δ 3.98 (s, 2H, CH$_2$), 5.92 (br s, 2-NH$_2$), 7.11 (d, J=8.4 Hz, 1H, H-8), 7.16-7.27 (m, 4H, H-2', H4', H-5', and H-6'), 7.21 (br s, 2H, 4-NH$_2$), 7.34 (d, J=8.4 Hz, 1H, H-7), 7.88 (s, 1H, H-5). Anal. Calcd for C$_{15}$H$_{13}$N$_4$Cl.0.2H$_2$O: C, 62.48, H, 4.68; N, 19.43; Cl, 12.29. Found: C, 62.32; H, 4.64; N, 19.38; Cl, 12.56.

EXAMPLE 4

Synthesis of 2-Amino-5-(4'-chlorobenzyl)benzonitrile (Scheme 2; Compound 10c; (R$_A$)$_i$=4-Cl).

From 9 (488 mg, 2 mmol) and 4-chlorobenzylzinc chloride (0.5 M in THF, 10 mL, 5 mmol) by the same method as 10a; white powder (243 mg, 59%): mp 91.5-93° C.; $^1$H NMR (DMSO-d$_6$) δ 3.79 (s, 2H, CH$_2$), 5.87 (br s, 2H, NH$_2$), 6.68 (d, J=8.0 Hz, 1H, H-3), 7.11 (d, J=8.0 Hz, 1H, H-4), 7.18 (d, J=8.4 Hz, 2H, H-2' and H-6'), 7.20 (s, 1, H-6),7.29 (d, J=8.4 Hz, 2H, H-3' and H-5').

Synthesis of 2,4-Diamino-6-(4'-chlorobenzyl)quinazoline (Scheme 2; Compound 8d; (R$_A$)$_i$=4-Cl).

From 10d (243 mg, 1 mmol) and chloroformamidine hydrochloride 456 mg, 4 mmol) at 130° C. for 15 min; white needles (107 mg, 37%): mp 224-225° C.; MS m/z 285.1, calcd 285.8 (M+1); IR (KBr) v 3340, 3160, 1615, 1565, 1510, 1490, 1450, 1400 cm$^{-1}$; $^1$H NMR (DMSO-d$_6$) δ 4.02 (s, 2H, CH$_2$), 5.89 (br s, 2-NH$_2$), 7.12 (d, J=8.8 Hz, 1H, H-8), 7.12 (s, J=8.8 Hz, 1H, H-8), 719 (br s, 2H, 2-NH$_2$), 7.25 (d, J=8.4 Hz, 2H, H-2' and H-6'), 7.32 (d, J=8.8 Hz, 1H, H-7), 7.34 (d, J=8.4 Hz, 2H, H-3' and H-5'), 7.88 (s, 1H, H-5). Anal. Calcd For C$_{15}$H$_{13}$N$_4$Cl0.2H$_2$O: C, 62.48; H, 4.68; N, 19.43; Cl, 12.29. Found: C, 62.52; H, 4.56; N, 19.63; Cl, 12.32.

EXAMPLE 5

Synthesis of 2-Amino-5-(3',4'-dichlorobenzyl)benzonitrile (Scheme 2; Compound 10e; $(R_A)_i$=3,4-Cl$_2$):

A suspension of active Zn metal in THF (0.76 M, 6.3 mL calculated to contain 4.8 mmol or a 20% theoretical excess) was placed in a thoroughly dried three-necked flask which was flushed continuously with a gentle stream of dry N$_2$. A solution of 3,4-dichlorobenzyl chloride (790 mg, 4 mmol) in dry THF (2 mL) was then added slowly to the flask at room temperature, and the reaction mixture was stirred at 68° C. for 10 h and left to stand for 3 h to allow the excess Zn metal to settle to the bottom. The dark-brown solution of organozinc reagent was transferred via a cannula using gentle N$_2$ pressure into another three-necked flask, to which was then added dropwise a solution of 9 (244 mg, 1 mmol) in dry THF (1 mL). Standard workup as for 10a afforded 10e as a pale-yellow powder (172 mg; 65%): mp 104-107° C.; $^1$H NMR (CDCl$_3$) δ 3.80 (s, 2H, CH$_2$), 4.35 (br s, 2H, NH$_2$), 6.68 (d, J=8.4 Hz, 1H-3), 6.97 (dd, J=8.0 Hz, 2.0 Hz, 1H, H-6'), 7.11 (s, J=8.4 Hz, H-4), 7.16 (s, 1H, H-6), 7.22 (d, J=2.0 Hz, 1H, H-2), 7.35 (d, J 8.0 Hz, 1H, H-5').

Synthesis of 2,4-Diamino-6-(3',4'-dichlorobenzyl)quinazoline (Scheme 2; Compound 8e; $(R_A)_i$=3,4-Cl$_2$):

From 10e (172 mg, 0.65 mmol) and chloroformamidine hydrochloride (298 mg, 2.6 mmol) at 130° C. for 15 min; white needles (78 mg, 37%): mp 150-151° C.; MS m/z 319.2, calcd 31.2 (M+1); IR (KBr) v 3310, 3180, 1620, 1560, 1510, 1470, 1445, 1400 cm$^{-1}$; $^1$H NMR (DMSO-d$_6$) δ 3.93 (s, 2H, CH$_2$), 5.89 (br s, 2H, 2-NH$_2$), 7.12 (d, J=8.4 Hz, 1H, H-8), 7.19 (br s, 2H, 4-NH$_2$), 7.22 (d, J=8.4 Hz, 1H, H-6'), 7.35 (d, J=8.4 Hz, 1H, H-7), 7.51 (s, 1H, H-2'), 7.54 (d, J=7.6 Hz, 1H, H-5'), 7.87 (s, 1H, H-5). Anal. Calcd. for C$_{15}$H$_{12}$N$_4$Cl$_2$0.1H$_2$O: C, 56.13; H, 3.83; N, 17.45; Cl, 22.09. Found: C, 56.21; H, 3.73; N, 17.27; Cl, 21.83.

EXAMPLE 6

Synthesis of 2-Amino-5-(4'-fluorobenzyl)benzonitrile (Scheme 2; Compound 10f; $(R_A)_i$=4-F):

From 9 (488 mg, 2 mmol) and 4-fluorobenzylzinc chloride (0.5 M in THF, 10 mL, 5 mmol) by the same method as 10a; pale-yellow powder (275 mg, 51%): mp 105-107° C.; $^1$H NMR (CDCl$_3$) δ 3.82 (s, 2H, CH$_2$), 4.32 (br, 2H, NH$_2$), 6.68 (d, J=8.8 Hz, 1H, H-3), 6.96-7.00 (m, 2H, 3'- and 5'-H), 7.08-7.14 (m, 3H, H-4, H-2', and H-6'), 7.17 (s, 1H, H-6).

Synthesis of 2,4-Diamino-6-(4'-fluorobenzyl)quinazoline (Scheme 2; Compound 8f; $(R_A)_i$=4-F):

From 10f (150 mg, 0.56 mmol) and chloroformamidine hydrochloride (255 mg, 2.24 mmol) at 120° C. for 30 min; white needles (97 mg, 65%): mp 214-216° C.; MS m/z 269.2, calcd 269.3 (M+1); IR (KBr) v 3310, 3180, 1610, 1550, 1500, 1440, 1400 cm$^{-1}$; $^1$H NMR (DMSO-d$_6$) δ 3.93 (s, 2H, CH$_2$), 5.86 (br, 2-NH$_2$), 7.08-7.14 (m, 3H, H-3', H-5', and H-8), 7.18 (br s, 2H, 4-NH$_2$), 7.25-7.28 (m, 2H, H-2'and H-6'), 7.32 (d, J=8.4 Hz, 1H, H-7), 7.88 (s, 1H, H-5). Anal. Calcd. for C$_{15}$H$_{13}$N$_4$F: C, 67.15; H, 4.88; N, 20.88; F, 7.08. Found: C, 6.98; H, 5.03; N, 20.81, F, 7.16.

EXAMPLE 7

Synthesis of 2-Amino-5-(2'-methoxybenzyl)benzonitrile (Scheme 2; Compound 10 g; $(R_A)_i$=2-OMe):

From 9 (610 mg, 2.5 mmol) and 2-methoxybenzylzinc chloride (0.5 M in THF, 10 mL, 5 mmol) by the same method as 10a; white powder (364 mg, 61%): mp 77.5-78.5° C.; $^1$H NMR (CDCl$_3$) δ 3.81 (s, 3H, OMe), 3.82 (s, 2H, CH$_2$), 4.25 (br s, 2H, NH$_2$), 6.64 (d, J=8.0 Hz, 1H, H-3), 6.85-6.88 (m, 2H, H-3' and H-5'), 7.06 (d, J=7.2 Hz, 1H, H-6'), 7.18-7.23 (m, 3H, H-4', H-4, and H-6).

Synthesis of 2,4-Diamino-6-(2'-methoxybenzyl)quinazoline (Scheme 2; Compound 8 g; $(R_A)_i$=2-OMe):

From log (190 mg, 0.8 mmol) and chloroformamidine hydrochloride (365 mg, 3.2 mmol) at 120° C. for 20 min; pale-yellow solid (127 mg, 57%): mp 214-215° C.; MS m/z 281.4, calcd 281.3 (M+1); IR (KBr) v 3340, 3180, 1610, 1560, 1500, 1450, 1400 cm$^{-1}$; $^1$H NMR (DMSO-d$_6$) δ 3.79 (s, 3H, Me), 3.89 (s, 2H, CH$_2$), 6.18 (br s, 2H, 2-NH$_2$), 6.85 (t, J=7.2 Hz, 1H, H-5'), 6.96 (d, J=8.4 Hz, 1H, H-3'), 7.05 (d, J=7.2 Hz, 1H, H-6'), 7.13 (d, J=8.4 Hz, 1H, H-8), 7.18 (t, J=7.6 Hz, 1H, H4'), 7.34 (d, J =8.4 Hz, 1H, H-7), 7.43 (br s, 2H, 4-NH$_2$), 7.89 (s, 1H; H-5). Anal. Calcd. for C$_{16}$H$_{16}$N$_4$O: H, 68.55; H, 5.73; N, 19.99. Found: C, 68.34; H, 5.58; N, 20.09.

EXAMPLE 8

Synthesis of 2-Amino-5-(3'-methoxybenzyl)benzonitrile (Scheme 2; Compound 10h; $(R_A)_i$=3-OMe):

From 9 (488 mg, 2 mmol) and 3-methoxybenzylzinc chloride (0.5 M in THF, 10 mL, 5 mmol) by the same method as 10a; white powder (274 mg, 49%): mp 81-82° C.; 1H NMR (CDCl$_3$) δ 3.81 (s, 2H, OMe), 3.82 (s, 2H, CH$_2$), 4.25 (br s, NH$_2$), 6.67 (d, J=8.0 Hz, 1H, H-3), 6.68 (s, 1H, H-2'), 6.72-6.77 (m, 2H, H4' and H-6'), 7.15 (d, J=8.0 Hz, H-4), 7.19 (s, 1H, H-6), 7.22 (t, J=7.6 Hz, 1H, H-5').

Synthesis of 2,4-Diamino-6-(3'-methoxybenzyl)quinazoline (Scheme 2; Compound 8h; $(R_A)_i$=3-OMe):

From 10h (238 mg, 1 mmol) and chloroformamidine hydrochloride (456 mg, 4 mmol) at 120° C. for 20 min; pale-yellow needles (124 mg, 60%): mp 207-209° C.; MS m/z 281.4, calcd 281.3 (M+1); IR (KBr) v 3415, 3350, 3110, 1650, 1600, 1550, 1500, 1425 cm$^{-1}$; $^1$H NMR (DMSO-d$_6$) δ 3.71 (s, 3H, OMe), 3.89 (s, 2H; CH$_2$), 6.03 (br s, 2-NH$_2$), 6.75 (d, J=7.2 Hz, 1H, H-4' or H-6'), 6.80 (d, J=7.2 Hz, 1H, H4' or H-6'), 6.81 (s, 1H, H-2'), 7.13 (d, J=8.8 Hz, 1H, H-8), 7.19 (t, J=7.6 Hz, 1H-5'), 7.32 (br s, 2H, 4-NH$_2$), 7.37 (d, J=8.4 Hz, 1H, H-7), 7.82 (s, 1H, H-5). Anal. Calcd. for C$_{16}$H$_{16}$N$_4$OC, 68.55; H, 5.73; N, 19.99. Found: C, 68.34; H, 5.91; N, 19.91.

EXAMPLE 9

Synthesis of 2-Amino-5-(4'-methoxybenzyl)benzonitrile (Scheme 2; Compound 10i; $(R_A)_1$=4-OMe):

From 9 (488 mg, 2 mmol) and 4-methoxybenzyl chloride (0.5 M in THF, 10 mL, 5.0 mmol) by the same method as 10a; white powder (239 mg, 43%): mp 72.5-73.5° C.; $^1$H NMR (CDCl$_3$) δ 3.79 (s, 5H, CH$_2$ and OMe), 4.28 (br s, NH$_2$), 6.66 (d, J=8.4 Hz, 1H, H-3), 6.83 (d, J=8.4 Hz, 2H, H-3' and H-5'), 7.05 (d, J=7.6 Hz, 2H, H-2' and H-6'), 7.14 (d, J=8.4 Hz, 1H, H4), 7.17 (s, 1H, H-6).

Synthesis of 2,4-Diamino-6-(4'-methoxybenzyl)quinazoline (Scheme 2; Compound 8i; $(R_A)_i$=4-OMe):

From 10i (238 mg, 1 mmol) and chloroformamidine hydrochloride (456 mg, 4 mmol) at 120° C. for 20 min; pale-yellow needles (124 mg, 60%):, mp 207-209° C.; MS n/z 281.4, calcd 281.2 (M+1); IR (KBr) v 3420, 3340, 3120, 1600, 1560, 1500, 1400 cm$^{-1}$; $^1$H NMR (DMSO-d$_6$) δ 3.70 (s, 3H, OMe), 3.86 (s, 2H, CH$_2$), 5.87 (br s, 2H, 2-NH$_2$), 6.84 (d, J=8.0 Hz, 2H, H-3' and H-5'), 7.10 (d, J=8.4, 1H, H-8), 7.14 (d, J=8.0 Hz, 2H, H-2' and H-6'), 7.18 (br s, 2H, 4-NH$_2$), 7.27 (d, J=8.8 Hz, H-7), 7.87 (s, 1H, H-5). Anal. Calcd. for $C_{16}H_{16}N_4O$: C, 68.55; H, 5.73; N, 19.99. Found: C, 68.62; H, 5.53; N, 20.12.

EXAMPLE 10

Synthesis of 2-Amino-5-(2',5'-dimethoxybenzyl)benzonitrile (Scheme 2; Compound 10j; $(R_A)_i$=2,5-(OMe)$_2$):

2,5-Dimethoxybenzylzinc chloride was prepared from 2,5-dimethoxybenzyl chloride (746 mg, 4 mmol) and reactive metallic zinc suspension (0.76 M in THF, 6.3 mL, 4.8 mmol). The supernatant was transferred via a cannula into a solution of 9 (366 g, 1.5 mmol) in THF, followed by the usual workup; pale-yellow powder (280 mg, 69%): mp 90-92° C.; $^1$H NMR (CDCl$_3$) δ 3.74 (s, 3H, OMe), 3.76 (s, 3H, OMe), 3.80 (s, 2H, CH$_2$), 4.66 (br s, 2H, NH$_2$), 6.63 (d, 1H, J=2.8 Hz, H-6'), 6.70 (d, J=8.4 Hz, 1H, H-3), 6.72 (dd, J=9.0 Hz, J=2.8 Hz, 1H, H4'), 6.80 (d, J=9.0 Hz, 1H, H-3;), 7.19 (d, J=8.4 Hz, 1H, H-4), 7.22 (s, 1H, H-6).

Synthesis of 2,4-Diamino-6-(2',5'-dimethoxybenzyl)quinazoline (Scheme 2; Compound 8j; $(R_A)_i$=2,5-(OMe)$_2$):

From 10j (120 mg, 0.45 mmol) and chloroformamidine hydrochloride (204 mg, 1.8 mmol) at 120° C. for 20 min; white crystals (65 mg, 46%): mp 190-192° C.; MS m/z 311.2, calcd 311.4 (M+1); IR (KBr) v 3360, 3180, 1610, 1560, 1490, 1440, 1400 cm$^{-1}$; $^1$H NMR (DMSO-d$_6$) δ 3.64 (s, 3H, OMe), 3.73 (s, 3H, OMe), 3.85 (s, 2H, CH$_2$), 5.81 (br s, 2H, 2-NH$_2$), 6.65 (d, J=3.2 Hz, 1H, H-6'); 6.73 (dd, J=9.0 Hz, 3.2 Hz, 1H, H-4'), 6.88 (d, J=9.0 Hz, 1H, H-3'), 7.10 (d, J=8.6, 1H, H-8), 7.15 (br s, 2H, 4-NH$_2$), 7.35 (dd, J=8.6 Hz, 2.0 Hz, 1H, H-7), 7.84 (d, J=2.0 Hz, 1H, H-5). Anal. Calcd. for $C_{17}H_{18}N_4O2$ 0.3H$_2$O: C, 64.66; H, 5.94; N, 17.74. Found: C, 64.62; H, 5.71; N, 17.74.

EXAMPLE 11

Synthesis of 2-Amino-5-(3',4'-dimethoxybenzyl)benzonitrile (Scheme 2; Compound 10k; $(R_A)_i$=3,4-(OMe)$_2$):

From 9 (488 mg, 2 mmol) and 3,4-dimethoxybenzylzinc chloride (0.5 M in THF, 10 mL, 5.0 mmol) by the same method as 10a; yellow oil (247 mg, 46%): $^1$H NMR (CDCl$_3$) δ 3.79 (s, 2H, CH$_2$), 3.83 (s, 3H, OMe), 3.86 (s, 3H, OMe), 4.21 (br s, NH$_2$), 6.65-6.82 (m, 4H, H-3, H-2', H-5', and H-6'), 7.15 (d, J=8.4 Hz, 1H, H-4),7.17 (s, 1H, H-6).

Synthesis of 2,4-Diamino-6-(3',4'-dimethoxybenzyl)quinazoline (Scheme 2; Compound 8k; $(R_A)_i$=3,4-(OMe)$_2$):

From 10k (120 mg, 0.45 mmol) and chloroformamidine hydrochloride (204 mg, 1.8 mmol) at 120° C. for 20 min; white crystals (61 mg, 43%): mp 215-217° C.; MS m/z 311.2, calcd 311.4 (M+1); IR (KBr) v 3350; 3180, 1610, 1550, 1500, 1440, 1400 cm$^{-1}$; $^1$H NMR (DMSO-d$_6$) δ 3.70 (s, 3H, OMe), 3.71 (s, 3H, OMe), 3.85 (s, 2H, CH$_2$), 5.85 (br s, 2H, 2-NH$_2$), 6.70 (dd, J=8.2 Hz, 1.8 Hz, 1H, H-6'); 6.84 (dd, J=1.8 Hz, 1 Hz, 1H, H-2'), 6.86 (d, J=8.2 Hz, 1H, H-5'), 7.11 (d, J=8.6, 1H, H-8), 7.18 (br s, 2H, 4-NH$_2$), 7.33 (dd, J=8.6 Hz, 1.8 Hz, 1H, H-7), 7.88 (d, J=1.8 Hz, 1H, H-5). Anal. Calcd. for $C_{17}H_{18}N_4O2$ 0.3H$_2$O: C, 64.66; H, 5.94; N, 17.74. Found: C, 64.35; H, 5.70; N, 17.78.

EXAMPLE 12

Synthesis of 2-Amino-5-(3',5'-dimethoxybenzyl)benzonitrile (Scheme 2; Compound 10; $(R_A)_i$=3,5-(OMe)$_2$):

From 9 (244 mg, 1 mmol) and 3,5-dimethoxybenzylazinc chloride (0.5 M in THF, 5 mL, 2.5 mmol) by the same method as 10a; pale-yellow powder (158 mg, 59%): mp 105-107° C.; $^1$H NMR (CDCl$_3$) δ 3.76 (s, 8H, CH$_2$, 3'-OMe, and 5'-OMe), 4.31 (br s, NH$_2$), 6.29-6.32 (m, 3H, H-2', H4', and H-6'), 6.8 (d, J=8.2 Hz, 1H, H-3), 7.14 (d, J=8.2 Hz, 1H, H-4), 7.19 (s, 1H, H-6).

Synthesis of 2,4-Diamino-6-(3',5'-dimethoxybenzyl)quinazoline (Scheme 2; Compound 8I; $(R_A)_i$=3,5-(OMe)):

From 101(120 mg, 0.45 mmol) and chloroformamidine hydrochloride (204 mg, 1.8 mmol) at 120° C. for 20 min; white crystals (57 mg, 41%): mp 230-232° C.; MS m/z 311.2, calcd 311.4 (M+1); IR (KBr) v 3360, 3160, 1610, 1560, 1490, 1450, 1400 cm$^{-1}$; $^1$H NMR (DMSO-d$_6$) δ 3.69 (s, 6H, OMe), 3.84 (s, 2H, CH$_2$), 5.84 (br s, 2H, 2-NH$_2$), 6.39 (d, J=2.4 Hz, 2H, H-2' and H-6'), 7.11 (d, J=8.6 Hz 1H, H-8), 7.17 (br s, 2H, 4-NH$_2$), 7.34 (dd, J=8.6 Hz, 2.0 Hz, 1H, H-7), 7.88 (d, J=2.2 Hz, 1H, H-5). Anal. Calcd. for $C_{17}H_{18}N_4O_2$): C, 65.79; H, 5.85; N, 18.05. Found: C, 65.53; H, 5.67; N, 18.12.

EXAMPLE 13

Synthesis of 2-Amino-5-(3',4',5'-trimethoxybenzyl)benzonitrile (Scheme 2; Compound 10m; $(R_A)_i$=3,4,5-(OMe)$_3$):

3,4,5-Trimethoxybenzylzinc chloride was prepared from 3,4,5-trimethoxybenzyl chloride (867 mg, 4 mmol) and reactive metallic zinc suspension (0.76 M in THF, 6.3 mL, 4.8 mmol). The supernatant was transferred via a cannula into a solution of 9 (244 g, 1 mmol) in THF, followed by the usual workup; pale-yellow oil (127 mg, 43%): $^1$H NMR (CDCl$_3$) δ 3.78 (s, 2H, CH$_2$), 3.81 (s, 6H, 3'- and 5'-OMe), 3.82 (s, 3H, 4'-OMe), 4.28 (br s, NH$_2$), 6.30 (s, 2H, H-2' and H-6'), 6.69 (d, J=8.4 Hz, 1H, H-3), 7.16 (d, J=8.4 Hz, 1H, H-4), 7.19 (s, 1H, H-6).

Synthesis of 2,4-Diamino-6-(3',4',5'-trimethoxybenzyl)quinazoline (Scheme 2; Compound 8m; $(R_A)_i$=3,4,5-(OMe)$_3$):

From 10m (82 mg, 0.28 mmol) and chloroformamidine hydrochloride (125 mg, 1.1 mmol) at 120° C. for 15 min; white crystals (47 mg, 49%): mp 219-221° C.; MS m/z 341.2, calcd 341.4 (M+1); IR (KBr) v 3380, 3180, 1620, 1560, 1500, 1450, 1400 cm$^{-1}$; $^1$H NMR (DMSO-d$_6$) δ 3.59 (s, 3H, 4'-OMe), 3.71 (s, 6H, 3'- and 5'-OMe), 3.84 (s, 2H, CH$_2$), 5.83 (br s, 2H, 2-NH$_2$), 6.54 (s, 2H, H-2' and H-6'), 7.10 (d, J=8.6 Hz, 1H, H-8), 7.14 (br s, 2H, 4NH$_2$), 7.35 (dd, J=8.6 Hz, 2.0 Hz, 1H, H-7), 7.88 (s, 1H, H-5). Anal. Calcd. for C$_{18}$H$_{20}$N$_4$O$_3$ 0.3H$_2$O: C, 62.52; H, 6.00; N, 16.20. Found: C, 62.14; H, 5.90; N, 16.13.

EXAMPLE 14

Synthesis of 2-Amino-5-(2'-naphthylmethyl)benzonitrile (Scheme 2; Compound 10n; CH$_2$Ph $(R_A)_i$=2-naphthylmethyl):

From 9 (488 mg, 2 mmol) and 2-naphth-ylmethylzinc chloride (0.5 M in THF, 10 mL, 5 mmol) by the same method as 10a; pale-yellow oil (327 mg, 63%): $^1$H NMR (CDCl$_3$) δ 4.01 (s, 2H, CH$_2$), 4.35 (br s, NH$_2$), 6.68 (d, J=8.0 Hz, 1H, H-3), 7.18 (d, J=8.0 Hz, H-4), 7.24 (s, 1H, H-6), 7.45-7.49 (m, 3H, H-4', H-5'- and H-8'), 7.59 (s, 1H, H-1'), 7.76-7.82 (m, 3H, H-3', H-6', H-7').

Synthesis of 2,4-Diamino-6-(2-naphthylmethyl)quinazoline (Scheme 2; Compound 8n; CH$_2$Ph $(R_A)_i$=2-naphthylmethyl):

From 10n (172 mg, 0.66 mmol) and chloroformamidine hydrochloride (300 mg, 2.64 mmol) at 120° C. for 20 min; white crystals (90 mg, 45%): mp 256-257° C.; MS m/z 301.3, calcd 301.4 (M+1); IR (KBr) v 3340, 3180, 1615, 1565, 1510, 1445, 1400 cm$^{-1}$; $^1$H NMR (DMSO-d$_6$) δ 4.04 (s, 2H, CH$_2$), 5.86 (br s, 2H, 2NH$_2$), 7.09 (d, J=8.2 Hz, 1H, H-8), 7.15 (br s, 2H, 4-NH$_2$), 7.33-7.46 (m, 4H, H-2', H-4', H-5', and H-7), 7.70 (s, 1H, H-1'), 7.78-7.85 (m, 3H, H-3', H-6', and H-7'), 7.93 (d, J=2.0 Hz, 2H, H-5). Anal. Calcd. for C$_{19}$H$_6$N$_4$0.3H$_2$O: C, 74.63; H, 5.47; N, 18.32. Found: C, 74.27; H, 5.37; N, 18.52.

All documents mentioned herein are incorporated herein by reference in their entirety.

The foregoing description of the invention is merely illustrative thereof, and it is understood that variations and modifications can be affected without departing from the spirit or scope of the invention as set forth in the following claims.

What is claimed is:

1. A compound according to Formula I:

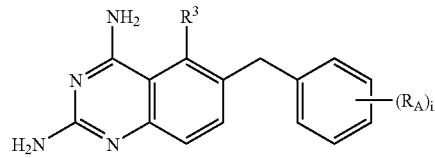

wherein:

$R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, chloro, fluoro, $C_{1-4}$fluoroalkyl, amino, mono and di($C_{1-6}$alkyl) amino, and nitrile; or two adjacent $R_A$ groups taken in combination form a group of the formula:

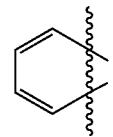

which may be optionally substituted;

$R^3$ is hydrogen; and i is an integer from 0 to about 5.

2. A compound of claim 1 wherein $R_A$ is independently selected at each occurrence of $R_A$ from the group consisting of hydrogen, chloro, and fluoro; or two adjacent $R_A$ groups taken in combination form a group of the formula:

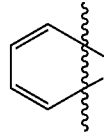

$R^3$ is hydrogen; and i is an integer from 0 to about 3.

3. A compound of claim 1 according to Formula I-A:

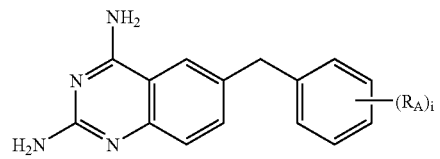

wherein
two adjacent $R_A$ groups taken in combination form a group of the formula:

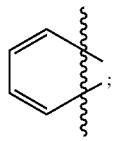

and
i is 2.

4. A pharmaceutical composition comprising a compound of any one of claims 1, 2, or 3 and a pharmaceutically acceptable carrier.

5. A method for treating a mammal suffering from a *Pneumocystis carinii* infection or a *Toxoplasma gondii* infection, comprising administering to the mammal an effective amount of a pharmaceutical composition of claim 4.

6. A method of claim 5 wherein the mammal is immunocompromised.

7. The method of claim 5, wherein the mammal is HIV-positive.

8. The method of claim 5, wherein the mammal is suffering from an acquired immune deficiency disorder.

9. The method of claim 5, wherein the mammal is suffering from an autoimmune disorder or disease.

10. The method of claim 5, wherein the mammal is suffering from *Toxoplasma gondii* infection.

11. The method of claim 5, wherein the mammal is a human.

12. The method of claim 5, wherein the mammal is suffering from *Pneumocystis carinii* infection.

13. A method of forming a compound according to Formula I:

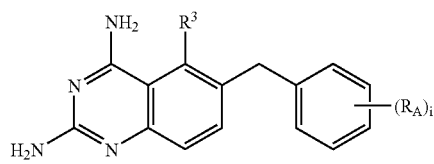

I the method comprising the steps of
contacting an aryl halide of the formula:

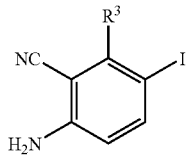

with at least one molar equivalent of a organozinc reagent, RZnY, and at least a catalytic amount of a palladium catalyst to form a C—C bond by a palladium mediated cross-coupling reaction; and contacting the product of the cross-coupling reaction with chloroformamidine under dry-fusion conditions to form a compound according to Formula I, wherein R is a benzyl residue of the formula —$CH_2C_6H_{5-i}(R_A)_i$;

$R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, $C_{1-4}$fluoroalkyl, amino, mono and di($C_{1-6}$ alkyl)amino, nitrile, optionally substituted aryloxy, optionally substituted heteroaryloxy, $C_{1-6}$alkylthio, optionally substituted arylthio, optionally substituted heteroarylthio, optionally substituted aryl acetoxy or optionally substituted heteroaryl acetoxy; or or two adjacent $R_A$ groups taken in combination form a group of the formula:

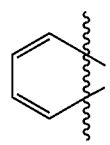

which may be optionally substituted;
$R^3$ is hydrogen; and
i is 0, 1, 2, or 3;
Y is Cl, Br, I, or triflate.

* * * * *